US00PP17299P3

(12) United States Plant Patent
Ui et al.

(10) Patent No.: US PP17,299 P3
(45) Date of Patent: Dec. 26, 2006

(54) ***CALIBRACHOA* PLANT NAMED 'KAKEGAWA S80'**

(50) Latin Name: ***Calibrachoa* sp.**
Varietal Denomination: Kakegawa S80

(75) Inventors: Akinobu Ui, Iwata (JP); Toshimi Ohga, Kikugawa (JP)

(73) Assignee: Sakata Seed Corporation, Yokohama (JP)

( * ) Notice: Subject to any disclaimer, the term of this patent is extended or adjusted under 35 U.S.C. 154(b) by 269 days.

(21) Appl. No.: 11/052,159

(22) Filed: Feb. 7, 2005

(65) Prior Publication Data

US 2006/0179532 P1 Aug. 10, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell

(74) *Attorney, Agent, or Firm*—Jondle & Associates P.C.

(57) ABSTRACT

'Kakegawa S80' is a new *Calibrachoa* cultivar particularly distinguished by having blue flowers with deep blue veins and a semi-creeping growth habit.

1 Drawing Sheet

Figure 1:
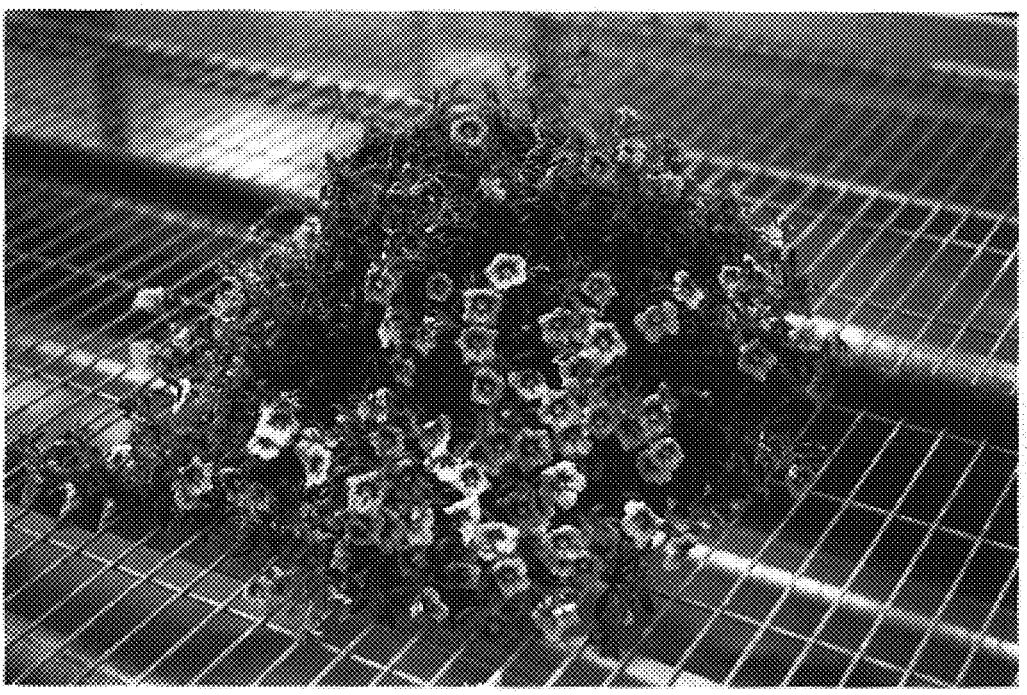

Genus and species: *Calibrachoa* sp.
Variety denomination: 'Kakegawa S80'.

BACKGROUND OF THE INVENTION

The present invention comprises a new and distinct cultivar of *Calibrachoa,* botanically known as *Calibrachoa* sp., and hereinafter referred to by the cultivar name 'Kakegawa S80'. It is characterized by having blue flowers with deep blue veins and a semi-creeping growth habit. The new cultivar originated from a hybridization made in Kakegawa, Japan in 1999. A proprietary *Calibrachoa* breeding line with red flowers and a semi-creeping growth habit The (Female) was crossed with a proprietary *Calibrachoa* breeding line with bronze vein flower color and a semi-upright growth habit (male).

In February 2000, $F_1$ seed from the above hybridization was sown in the greenhouse. Four single-plant selections were made based on their bronze vein flower color and upright growth habit and intercrossed to produce $F_2$ seed. In August 2000, $F_2$ seed was sown and 120 total plants were evaluated. Three single-plant selections with bronze vein flower color and a semi-creeping growth habit were selected and intercrossed to produce $F_3$ seed. In February 2001, $F_3$ seed was sown in the greenhouse. Four single-plant selections were made based on the intensity of their flower vein color and intercrossed to produce $F_4$ seed. In August 2001, $F_4$ seed was sown in the greenhouse. Two single-plant selections were made based on their blue vein flower color and crossed to produce $F_5$ seed. In February 2002, $F_5$ seed was sown in the greenhouse. One single-plant selection was made based on its deep blue vein flower color and semi-creeping growth habit and asexually propagated through rooted plant cuttings in both Kakegawa, Japan and Salinas, Calif. 'Kakegawa S80' has been shown to reproduce true to type in successive generations of asexual propagation.

Description of the Genus *Calibrachoa* Llave & Lex

The genus *Petunia* was originally established in 1803 by A. L. Jussieu, who described both *P. parviflora* and *P. nyctaginiflora* as type species. Using a non-horticultural system that selected the first mentioned species as the type species (lectotype), N. L. Britton and H. A. Brown declared *P. parviflora* as the type species for *Petunia* in 1913.

During the 1980's and 1990, H. J. Wijsman published a series of articles regarding the ancestry of *P. hybrida,* the Garden *Petunia,* and the inter-relationship of several species classified as *Petunia.* These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the *Petunia* genus, Wijsman and J. H. de Jong proposed transferring the 14 chromosome species to the genus *Stimoryne.* Horticulturists opposed reclassifying the Garden *Petunia* and in 1986, Wijsman proposed the alternative of making *P. nyctaginiflora* the lectotype species for *Petunia* and transferring the 18 chromosome species to another genus. The I. N. G. Committee adopted this proposal. By 1990 Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current *Petunia* and *Calibrachoa* species is still in progress. New species are also being identified. Consequently a proper description has not been written for the *Calibrachoa* genus. *Calibrachoa* can, however, be distinguished from *Petunia* based on the higher chromosome number, chromosome morphology, plant branching habit and type of flower bud aestivation. Whereas *Petunia* species bear a flower peduncle and one new stem from a node, *Calibrachoa* bear a flower peduncle and three stems. *Petunia* species have a cochlear corolla bud, and a single outermost petal covers the other four, radially folded and terminally contorted petals. *Calibrachoa* flower buds are flat with all five petals linearly folded and the two lower petals forming a cover around the three other petals and fused together.

DESCRIPTION OF PHOTOGRAPHS

This new *Calibrachoa* plant is illustrated by the accompanying photographs which show the plant's form, foliage and flowers. The colors shown are as true as can be reasonably obtained by conventional photographic procedures.

FIG. 1. shows overall plant habit.

Figure 2:
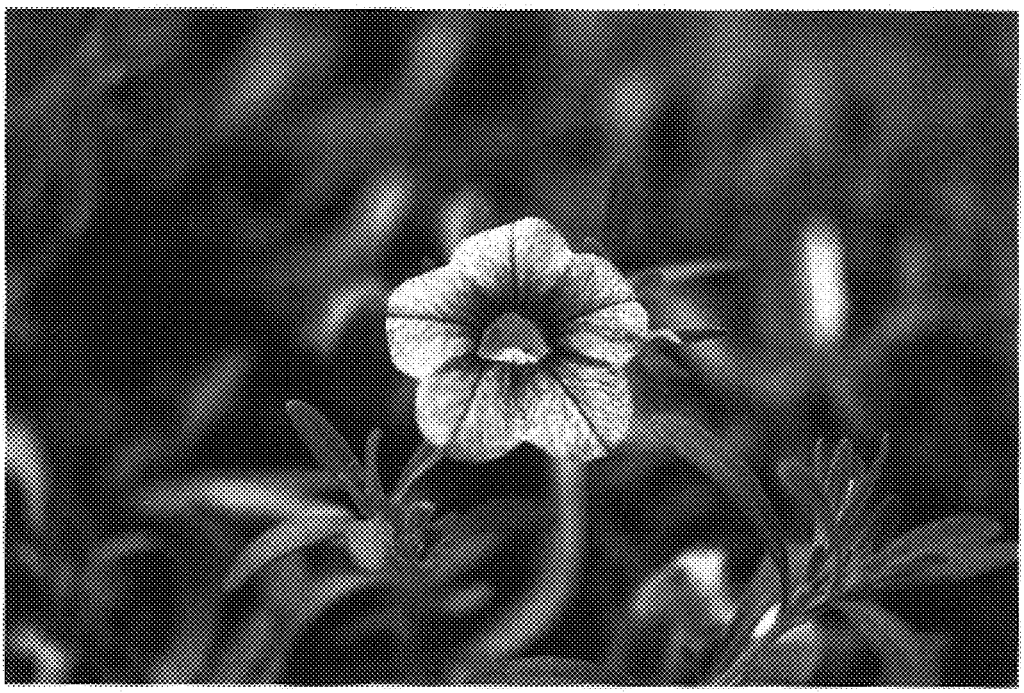

FIG. 2. shows the mature flower.

DESCRIPTION OF THE NEW CULTIVAR

The following detailed description sets forth the distinctive characteristics of 'Kakegawa S80'. The data which define these characteristics were collected from asexual reproductions carried out in Salinas, Calif. The detailed description was taken from plants grown under greenhouse conditions for approximately 4 months from transplanting of rooted cuttings. Color references are to The R.H.S. Color Chart of The Royal Horticultural Society of London (R.H.S.), 4$^{th}$ Edition.

DETAILED BOTANICAL DESCRIPTION

Classification:
- *Family.*—Solanaceae.
- *Species.*—*Calibrachoa* sp. Cultivar 'Kakegawa S80'.
- *Common name.*—*Calibrachoa.*

Parentage:
- *Male.*—Unnamed and unknown proprietary *Calibrachoa* breeding line.
- *Female.*—Unnamed and unknown proprietary *Calibrachoa* breeding line.

Plant description:
- *Life cycle.*—Tender Perennial.
- *Form.*—Freely branching.
- *Habit.*—Semi-decumbent (mounding).
- *Height.*—12 cm as measured from soil level to top of plant.
- *Spread.*—38 cm.

Propagation:
- *Type cuttings.*—Vegetative cuttings.
- *Time to produce a rooted cutting.*—5–6 weeks.
- *Time to bloom from propagation.*—10 weeks after root development.

Environmental conditions for plant growth: The terminal 1.0–1.5 inches of actively growing stems were excised and the base of each cutting dipped for one to two seconds in a 1:9 solution of DIP 'N GROW root inducing solution immediately prior to placing the cutting into a cell tray. The cell tray contained a moistened peat moss-based growing medium. The cuttings were misted with water from overhead for 10 seconds every 30 minutes until sufficient roots were formed. Rooted cuttings were transplanted and grown individually in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow-release fertilizer containing 20% nitrogen, 10% phosphorous and 18% potassium. The typical average air temperature was 24° C.

Stems:
- *Stem color.*—RHS 141C (green).
- *Anthocyanin color.*—RHS 79B (purple).
- *Pubescence.*—Heavy.
- *Pubescence color.*—RHS 155A (white).
- *Stem description.*—Ancipital (round).
- *Stem diameter.*—0.5 cm.
- *Stem length.*—1.5–1.8 cm.
- *Internode length.*—0.8–1.0 cm.

Leaves:
- *Leaf arrangement.*—Alternate.
- *Leaf shape.*—Elliptical.
- *Leaf apex.*—Mucronate.
- *Leaf base.*—Decurrent.
- *Leaf margin.*—Entire.
- *Leaf surface.*—Rough, dull.
- *Leaf surface pubescence.*—Slight.
- *Pubescence color.*—RHS 155A (white).
- *Venation.*—Pinnate.
- *Leaf length.*—2.0 cm.
- *Leaf width.*—0.5 cm.
- *Leaf color.*—Upper surface: RHS 137A (green). Lower surface: RHS 137B (green).
- *Petiole length.*—1.4–2.0 cm.
- *Petiole color.*—RHS 144A (yellow-green).

Inflorescence:
- *Flowering habit.*—Indeterminate.
- *Flower type.*—Solitary.
- *Flowering requirements.*—Will flower so long as day length is greater than 12 hours and temperature exceeds 13° C.
- *Duration of flowers.*—About 5 days.
- *Corolla shape.*—Flowers are funnel-shaped with five fused petals and five fissures dividing the petals.
- *Fragrance.*—Absent.

Flower buds:
- *Bud surface.*—Pubescent.
- *Bud length.*—1.0 cm.
- *Bud diameter.*—0.3 cm.
- *Bud shape.*—Ovate.
- *Bud color.*—RHS 150B (yellow-green).
- *Peduncle length.*—1.2 mm–1.7 mm.
- *Peduncle color.*—RHS 144A (yellow-green).

Flower description:
- *Flower depth.*—2.0 cm.
- *Flower tube length.*—1.0 cm.
- *Flower tube diameter.*—0.3–0.4 cm.
- *Flower diameter.*—2.8 cm.
- *Calyx.*—5 sepals, free.
- *Sepals.*—Shape: Lanceolate. Apex: Mucronate. Margin: Entire. Sepal color: Upper surface: RHS 137B (green). Lower surface: RHS 137C (green).
- *Petal shape.*—Spatulate.
- *Petal length.*—1.4 cm.
- *Petal width.*—1.2 cm.
- *Petal apex.*—Between truncate and obtuse.
- *Petal margin.*—Entire.
- *Petal texture.*—Glabrous.
- *Petal color.*—Lobe color: Upper surface: RHS 93B (violet-blue) at lobe base quickly fading to RHS 155A (white) with RHS 82A (purple-violet) midvein and RHS 93B (violet-blue) veins. Lower surface: RHS 91D (violet-blue) with a RHS 79A (purple) midvein. Corolla tube color: Inner: RHS 13B (yellow) with RHS 79C (purple) stripes and veins. Outer: RHS 6C (yellow) with RHS 79C (purple) stripes and veins.

Reproductive organs:

*Stamen number.*—5, free.

*Stamen color.*—RHS 144C (yellow-green).

*Pollen color.*—RHS 7B (yellow).

*Ovary.*—Superior.

*Pistil number.*—1 per inflorescence.

*Pistil length.*—1.25 mm.

*Stigma color.*—RHS 144A (yellow-green).

*Style length.*—0.81 mm.

*Style color.*—RHS 144C (yellow-green).

Disease and insect resistance: 'Kakegawa S80' has excellent resistance to rain, heat and drought, although it will not tolerate temperatures below 10° C. 'Kakegawa S80' is susceptible to *Botrytis,* powdery mildew, various stem and root rots, and certain viruses, such as Tobacco Mosiac Virus and *Impatiens* Necrotic Spotted Virus. 'Kakegawa S80' is also susceptible to aphids, leafminers, whiteflies and various *Lepidoptera.*

Comparison with Known Cultivars

*Calibrachoa* 'Kakegawa S80' is a distinct variety of *Calibrachoa* due to its blue flower color with violet-blue veins. 'Kakegawa S80' is distinguished from known cultivars mainly by flower color and growth habit as shown in Table 1 below.

TABLE 1

| Characteristic | 'Kakegawa S80' | '9B-58C' | '7BC-42A-1' |
|---|---|---|---|
| Flower color | Blue with deep blue veins | Red | Dark orange |
| Growth habit | Semi-creeping | Semi-creeping | Semi-erect |

'Kakegawa S80' is most similar to the variety 'Liricashower Blue' (U.S. Plant Pat. No. 9,885); however, there are differences in flower petal color and corolla tube color as described in Table 2 below.

TABLE 2

| Characteristic | 'Kakegawa S80' | 'Liricashower Blue' |
|---|---|---|
| Petal color, upper surface | RHS 93B (violet-blue) at lobe base quickly fading to RHS 155A (white) with RHS 82A (purple-violet) midvein and RHS 93B (violet-blue) veins | RHS 88A (blue) fading slightly with age to RHS 88B (blue) |
| Outer corolla tube color | RHS 6C (yellow) with RHS 79C (purple) veins | Pale white to cream to light green-yellow tones |

We claim:

1. A new and distinct cultivar of *Calibrachoa* plant as shown and described herein.

* * * * *